United States Patent
Shay

(10) Patent No.: US 8,507,720 B2
(45) Date of Patent: Aug. 13, 2013

(54) TITANIA-ALUMINA SUPPORTED PALLADIUM CATALYST

(75) Inventor: Daniel Travis Shay, Glen Mills, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 12/657,893

(22) Filed: Jan. 29, 2010

(65) Prior Publication Data

US 2011/0190533 A1   Aug. 4, 2011

(51) Int. Cl.
- C07C 67/02    (2006.01)
- B01J 23/00    (2006.01)
- B01J 21/00    (2006.01)
- B01J 20/00    (2006.01)

(52) U.S. Cl.
USPC ........... 560/261; 502/159; 502/327; 502/330; 502/332; 502/333; 502/339; 502/351; 502/355; 502/415; 502/439

(58) Field of Classification Search
USPC .......... 502/327, 330, 332, 333, 339, 351, 502/355, 415, 439, 159; 560/261
See application file for complete search history.

(56) References Cited

U.S. PATENT DOCUMENTS

| | | | |
|---|---|---|---|
| 3,743,607 A | 7/1973 | Sennewald et al. | |
| 3,775,342 A | 11/1973 | Kronig et al. | |
| 4,046,832 A | 9/1977 | Nowak et al. | |
| 4,552,860 A | 11/1985 | Murib | |
| 4,992,406 A * | 2/1991 | Mauldin et al. | 502/304 |
| 5,140,050 A * | 8/1992 | Mauldin et al. | 518/715 |
| 5,194,417 A | 3/1993 | Smith et al. | |
| 5,336,802 A | 8/1994 | Smith et al. | |
| 5,783,726 A | 7/1998 | Lemanski et al. | |
| 5,804,296 A * | 9/1998 | Itoh et al. | 428/326 |
| 5,859,287 A | 1/1999 | Nicolau et al. | |
| 5,884,138 A | 3/1999 | Chalasani et al. | |
| 5,977,012 A | 11/1999 | Kharas et al. | |
| 6,022,823 A | 2/2000 | Augustine et al. | |
| 6,040,474 A | 3/2000 | Jobson et al. | |
| 6,107,514 A | 8/2000 | Nicolau et al. | |
| 6,114,574 A | 9/2000 | Sen et al. | |
| 6,180,821 B1 | 1/2001 | Jobson et al. | |
| 6,225,496 B1 | 5/2001 | Baker et al. | |
| 6,274,531 B1 | 8/2001 | Nicolau et al. | |
| 6,316,383 B1 | 11/2001 | Tacke et al. | |

(Continued)

FOREIGN PATENT DOCUMENTS

| EP | 0455307 A1 | 11/1991 |
|---|---|---|
| EP | 0516262 A1 | 11/1991 |

(Continued)

OTHER PUBLICATIONS

C. E. Capes, "Particle Size Enlargement," *Handbook of Powder Technology*, Elsevier Scientific Publishing Company, 1980, vol. 1, pp. 112-122.

(Continued)

*Primary Examiner* — Cam N. Nguyen

(57) ABSTRACT

A catalyst comprising palladium supported on a titania-alumina extrudate is disclosed. The extrudate comprises at least 80 wt % titania and 0.1 to 15 wt % alumina. A palladium catalyst prepared from the titania-alumina extrudate has significantly higher crush strength. Its catalytic performance in vinyl acetate production is improved.

15 Claims, 1 Drawing Sheet

(56) References Cited

U.S. PATENT DOCUMENTS

| | | | |
|---|---|---|---|
| 6,376,706 B2 | 4/2002 | Kitchen et al. | |
| 6,420,595 B1 | 7/2002 | Hallinan et al. | |
| 6,632,973 B1 | 10/2003 | Miyake et al. | |
| 6,696,596 B1 | 2/2004 | Herzog et al. | |
| 6,709,570 B1 | 3/2004 | Van Crijnen-Beers | |
| 6,797,669 B2 * | 9/2004 | Zhang et al. | 502/339 |
| 6,803,340 B2 * | 10/2004 | Lee et al. | 502/309 |
| 6,849,243 B1 | 2/2005 | Hagemeyer et al. | |
| 6,987,200 B2 | 1/2006 | Hagemeyer et al. | |
| 6,992,040 B2 * | 1/2006 | Muller et al. | 502/327 |
| 7,387,981 B1 | 6/2008 | Kaminsky et al. | |
| 7,491,843 B2 | 2/2009 | Jobson et al. | |
| 7,514,476 B2 | 4/2009 | Parasher et al. | |
| 7,521,393 B2 * | 4/2009 | Blankenship et al. | 502/330 |
| 7,556,793 B2 | 7/2009 | Dahar | |
| 7,612,244 B2 * | 11/2009 | Strebelle et al. | 570/244 |
| 7,638,459 B2 * | 12/2009 | Rende et al. | 502/300 |
| 7,648,936 B2 | 1/2010 | Morales et al. | |
| 7,674,744 B2 * | 3/2010 | Shiratori et al. | 502/327 |
| 7,745,370 B2 * | 6/2010 | Blankenship et al. | 502/262 |
| 7,811,968 B2 * | 10/2010 | Augustine | 502/330 |
| 7,820,583 B2 * | 10/2010 | Fu et al. | 502/209 |
| 7,842,641 B2 * | 11/2010 | Fu et al. | 502/242 |
| 7,910,517 B2 * | 3/2011 | Schubert et al. | 502/346 |
| 8,178,715 B2 | 5/2012 | Johnston et al. | |
| 8,273,682 B2 | 9/2012 | Shay | |
| 8,329,611 B2 | 12/2012 | Shay | |
| 2001/0025009 A1 | 9/2001 | Fischer et al. | |
| 2001/0056201 A1 | 12/2001 | Couves et al. | |
| 2002/0025905 A1 | 2/2002 | Harris et al. | |
| 2002/0028966 A1 | 3/2002 | Blum et al. | |
| 2002/0062039 A1 | 5/2002 | Salem et al. | |
| 2002/0165092 A1 | 11/2002 | Zhang | |
| 2005/0095189 A1 | 5/2005 | Brey et al. | |
| 2005/0150845 A1 | 7/2005 | Hashimoto et al. | |
| 2005/0255021 A1 | 11/2005 | Di Francesco | |
| 2005/0261125 A1 | 11/2005 | Sagae | |
| 2007/0179310 A1 | 8/2007 | Augustine | |
| 2007/0214759 A1 | 9/2007 | Merkel | |
| 2008/0146721 A1 | 6/2008 | Kaminsky et al. | |
| 2008/0153692 A1 | 6/2008 | Kimmich et al. | |
| 2008/0281122 A1 | 11/2008 | Augustine | |
| 2008/0287289 A1 | 11/2008 | Wang et al. | |
| 2008/0287703 A1 | 11/2008 | Wang et al. | |
| 2009/0093361 A1 | 4/2009 | Sakatani et al. | |
| 2009/0093653 A1 | 4/2009 | Mayer et al. | |
| 2010/0099552 A1 * | 4/2010 | Fu et al. | 502/209 |
| 2010/0121100 A1 | 5/2010 | Shay | |
| 2010/0168466 A1 | 7/2010 | Johnston et al. | |
| 2011/0087047 A1 | 4/2011 | Hallinan et al. | |
| 2011/0144380 A1 | 6/2011 | Shay | |
| 2011/0190533 A1 | 8/2011 | Shay | |
| 2011/0306748 A1 | 12/2011 | Shay | |

FOREIGN PATENT DOCUMENTS

| | | |
|---|---|---|
| JP | 2001286733 A | 10/2001 |
| WO | WO2006094746 | 9/2006 |
| WO | 2006/127136 A1 | 11/2006 |
| WO | 2009/134398 A2 | 11/2009 |
| WO | 2011075278 | 6/2011 |

OTHER PUBLICATIONS

C. E. Capes, "Particle Size Enlargement," Handbook of Powder Technology, vol. 1, Elsevier Scientific Publishing Company, 1980, pp. 112-122.

Aida Guitierrez-Alejandre, A Vibrational and Spectroscopic Study, WO3/TiO2-Al2O3 of Catalyst Precursors, Langmuir, vol. 14, No. 3, 1998, pp. 630-639.

Alvin B. Stiles, "Chapter 3. Supports Other Than Alumina," Catalyst Supports and Supported Catalysts, Butterworths Publishers, 1987, pp. 57-85.

David B. Braun and Meyer R. Rosen, Rheology Modifiers Handbook; Practical Use and Application, William Andrew Publishing, 2000, pp. 109-131.

Mu, X., the Preparation of Pd/SiO2 Catalyst by Chemical Vapor Deposition in a Fluidized-Bed Reactor, Applied Catalysis A: General 248 (2003), pp. 85-95.

* cited by examiner

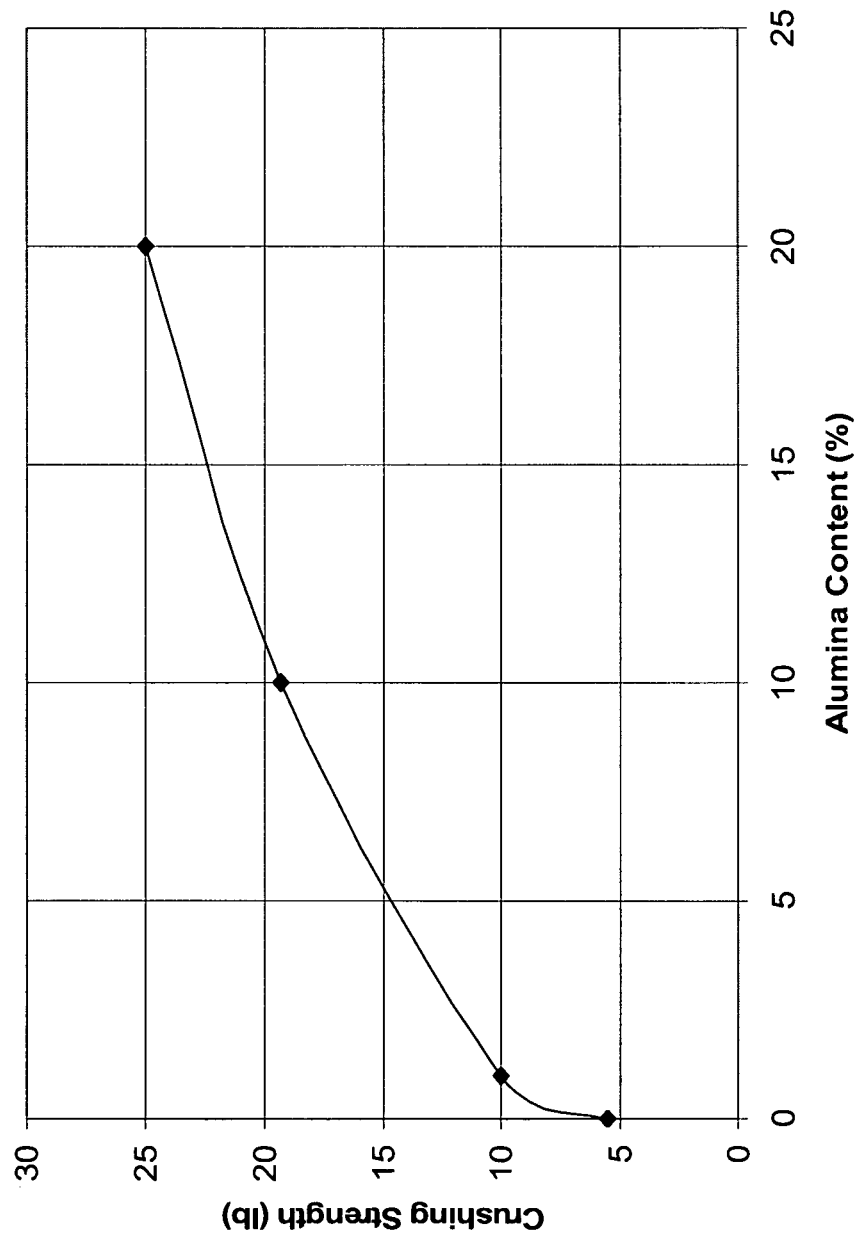

TITANIA-ALUMINA SUPPORTED PALLADIUM CATALYST

FIELD OF THE INVENTION

The invention relates to a catalyst comprising palladium supported on a titania-alumina carrier.

BACKGROUND OF THE INVENTION

Catalysts containing palladium and a Group 11 metal supported on titania are useful in catalyzing acetoxylation of olefins, see, for example, U.S. Pat. No. 6,022,823, U.S. Pat. Appl. Pub. Nos. 2008/0146721 and 2008/0281122. However, a catalyst prepared from a titania extrudate generally has low crush strength. Catalysts with low crush strengths tend to attrit in a reactor, cause pressure drops in is a reactor, and plug process lines. There is a need to develop catalysts with high crush strength.

SUMMARY OF THE INVENTION

The invention is a catalyst comprising palladium supported on an extrudate. The extrudate comprises at least 80 wt % titania and 0.1 to 15 wt % alumina. A palladium catalyst prepared from a titania-alumina extrudate has significantly higher crush strength and good activity.

BRIEF DESCRIPTION OF DRAWINGS

FIG. 1 shows the correlation of the crush strengths of catalysts supported on titania-alumina extrudates and their alumina contents.

DETAILED DESCRIPTION OF THE INVENTION

This invention is a catalyst comprising palladium supported on a titania-alumina extrudate comprising at least 80 wt % titania and 0.1 to 15 wt % alumina. Preferably it comprises at least 85 wt %, more preferably at least 90 wt % titania, and 0.2 to 10 wt %, more preferably 0.5 to 5 wt % alumina.

To prepare the extrudate, titania or a titania precursor and alumina or an alumina precursor are mixed using any suitable method, such as mulling or kneading to form a paste. Commercially, titania may be produced by the chloride process, the sulfate process, the hydrothermal process, or the flame hydrolysis of titanium tetrachloride. Examples of suitable titanias include TiONA® DT-51, DT-52, DT-51D, DT-40, and DT-20 of Millennium Inorganic Chemicals. Suitable titania precursors include titanium salts, titanium halides, titanium alkoxides, titanium oxyhalides, and the like. Examples of suitable aluminas include DISPERAL®, PURAL®, PURALOX® of Sasol. Suitable alumina precursors include aluminium alkoxides and aluminium salts.

A solvent is used to form the paste. Examples of suitable solvents include water, alcohols, esters, amides, and the like, and mixtures thereof. Preferred solvents are water and alcohols. Water is the most preferred.

An extrusion aid may be used to form the paste. Suitable extrusion aids is include carboxylic acids, alkyl ammonium compounds, amino alcohols, cellulose, cellulose derivatives, starch, polyacrylates, polymethacrylates, poly(vinyl alcohol)s, poly(vinylpyrrolidone)s, poly(amino acid)s, polyethers, poly(tetrahydrofuran)s, metal carboxylates, and the like, and mixtures thereof. Examples of cellulose derivatives include sodium carboxyalkylcellulose, hydroxyalkylcellulose, and methylcellulose. Preferably the extrusion aid includes a combination of a sodium carboxyalkylcellulose and a hydroxyalkylcellulose. A carboxyalkylcellulose to hydroxyalkylcellulose weight ratio of 3:1 to 1:1 is more preferred.

Carboxyalkyl cellulose is a cellulose derivative with carboxyalkyl groups bound to some of the hydroxyl groups of the glucopyranose monomers that make up the cellulose backbone. It is often used as its sodium salt, sodium carboxyalkyl cellulose. Preferably, a sodium salt of carboxymethyl cellulose is used.

Hydroxyalkyl cellulose is a derivative of cellulose in which some of the hydroxyl groups in the repeating glucose units have been hydroxyalkylated. Preferably the hydroxyalkyl group is 2-hydroxyethyl or 2-hydroxypropyl group.

Extrusion of the paste produces an extrudate, which contains solvent and possibly extrusion aids. Extrusion is a manufacturing process in which a paste is pushed through a die or an orifice to create long objects of a fixed cross-section. Extrusion is commonly used to process plastics or food, and to form adsorbents or catalysts. Any conventional extruder may be used. The extrudate usually has a diameter of 0.5 to 10 mm, in particular from 1 to 5 mm. A suitable screw-type extruder is described in "Particle Size Enlargement," Handbook of Powder Technology, vol. 1 (1980) pp. 112-22.

The extrudate is calcined. Preferably, the calcination is carried out in an oxygen-containing atmosphere to burn off the organic materials (e.g., residual solvent, extrusion aids, and the like) contained in the extrudate. The calcination may be carried out at 400 to 1000° C., more preferably from 450 to 700° C. Sometimes, it is beneficial to initially calcine the extrudate in an inert atmosphere (e.g., nitrogen, helium) to thermally decompose the organic compounds contained in the extrudate, and then burn off the organic materials in an oxygen-containing atmosphere.

The catalyst generally contains from 0.05 to 3 wt % palladium and optionally a Group 11 metal in the amount of from 0.05 to 1.5 wt %. More preferably, the catalyst contains from 0.5 to 1.5 wt % palladium and from 0.25 to 0.75 wt % gold.

To prepare the catalyst, the calcined extrudate is typically treated with an aqueous solution of a palladium salt. The concentrations and the amounts of solutions used depend on the desired concentrations of palladium in the final catalyst. Water is then removed leaving the palladium salt deposited on the extrudate. Suitable palladium salts include palladium chloride, sodium chloropalladite, palladium nitrate, and palladium sulfate. A Group 11 metal salt may be added to the extrudate along with the palladium addition or in a separate step. For example, an aqueous solution of auric chloride, tetrachloroauric acid, sodium tetrachloroaurate, and the like may be used.

The impregnated extrudate is calcined at a temperature in the range of 100° C. to 600° C. in an inert or oxidizing gas such as helium, nitrogen, argon, neon, nitrogen oxides, oxygen, air, carbon dioxide, and the like. Mixtures of the aforementioned gases may also be used. Preferably the calcination is carried out in nitrogen, oxygen or air, or mixtures thereof, typically for 0.1 and 5 h.

Following the calcination, the resulting product is reduced to convert at least a portion of the palladium, and the Group 11 metal if used, to produce a reduced catalyst. In general, any known procedure using conventional reducing agents such as ammonia, carbon monoxide, hydrogen, hydrocarbons, olefins, aldehydes, alcohols, hydrazine, primary amines, carboxylic acids, carboxylic acid salts, and carboxylic acid esters can be used. Hydrogen, ethylene, propylene, alkaline hydrazine, and alkaline formaldehyde are highly useful reducing agents; and ethylene and hydrogen are particularly preferred. While pure hydrogen may be used, it is more common to use a mixture of hydrogen and an inert gas such as nitrogen, helium, argon, or the like. These mixtures generally contain up to about 50 volume percent (vol. %) hydrogen and, more typically, are comprised of about 5 to 25 vol. % hydrogen and 75 to 95 vol. % inert gas. Reduction times typically vary from 0.1 to 5 h. Temperatures employed for the reduction can range from 20 to 600° C.

The catalyst may be used for the acetoxylation of an olefin, such as ethylene or propylene, to produce an acetoxylated olefin such as vinyl acetate or allyl acetate. Preferably, a promoted catalyst, which can be produced by adding an activator to the reduced catalyst, is used in the acetoxylation reaction. An activator is an alkali or alkaline earth metal compound, examples of which are hydroxides, acetates, nitrates, carbonates, and bicarbonates of potassium, sodium, cesium, magnesium, barium, and the like. Potassium salts are preferred activators. The activator content may be in the range of 0.1 to 15 wt %, preferably 0.5 to 10 wt % of the catalyst.

The invention also includes a process for preparing vinyl acetate, comprising reacting a feed comprising ethylene, oxygen, and acetic acid in the presence of the catalyst.

The feed typically comprises 20 to 70 mol % ethylene, 2 to 8 mol % oxygen, and 2 to 20 mol % acetic acid. The feed may comprise a diluent. Examples of suitable diluents include propane, nitrogen, helium, argon, carbon dioxide, the like, and mixtures thereof.

The reaction is generally performed in a fixed bed reactor at a temperature in the range of 100 to 250° C., preferably 125 to 200° C. and under a pressure of 15 to 500 psig.

Example 1

Extrudate Preparation and Characterization

D-T51 titania (178.2 g), alumina (DISPERAL® P2, available from Sasol, 1.8 g), a high-purity WALOCEL™ C sodium carboxymethyl cellulose (The Dow Chemical Company, 3.8 g), poly(ethylene oxide) (MW=100,000, 3.4 g), and a cellulose derivative (METHOCEL™ K4M from The Dow Chemical Company, 1.8 g) are mixed for 5 min. Water (100 g), an aqueous ammonium hydroxide (14.8 M, 10.5 g), and benzyl alcohol (1.3 g) are added into the mixture and further mixed to produce a paste. The paste is placed in the hopper of a Bonnot 1-inch extruder (The Bonnot Company) equipped with a die face of 2 holes with a diameter of ⅛ inch.

The extrudates are collected and dried in air at 80° C. for 12 h, then calcined in air. The calcination temperature is raised from room temperature to 500° C. at a rate of 2° C./min, held at 500° C. for 2 h, raised from 500° C. to 700° C. at a rate of 10° C./min, is held at 700° C. for 3 h, then lowered to room temperature.

Pd—Au Catalyst:

$NaHCO_3$ powder (2.7 g) is slowly added to an aqueous solution containing $Na_2PdCl_4.3H_2O$ (3.1 g), $NaAuCl_4.2H_2O$ (1.1 g), and water (23.5 g). The mixture is stirred at room temperature for 10 min. The solution is sprayed with a pipette on the calcined extrudates (100 g) while they are being tumbled in a rotating flask. Once the impregnation is finished, the rotating flask is heated to about 100° C. with a heat gun. The impregnated extrudates are tumbled for another 30 min at 100° C., then placed in an oven at 80° C. for 2 h before they are cooled to room temperature.

The dried extrudates are washed with warm water (50 to 80° C.) until no chloride can be detected by mixing the wash filtrate solution with a 1 wt % silver nitrate solution to observe precipitation. After washing is finished, the catalyst is dried at 80 to 100° C. to remove water. Then they are heated at 230° C. for 3 h in air, and at 230° C. for 30 min under a nitrogen flow. The temperature is raised to 500° C. under a flow of 10 mol % hydrogen in nitrogen gas, and held for 3 h before it is cooled to room temperature.

The extrudates are washed with an aqueous solution containing 10 wt % potassium acetate and 1 wt % potassium hydroxide (1 L). The washed extrudates are dried under nitrogen at 125° C. for 2 h. A palladium-gold catalyst is obtained. It contains 0.93 wt % Pd, 0.54 wt % Au, and 1.5 wt % K.

Some physical properties of the catalyst are listed in Table 1. The crush strength of the catalyst is measured with a Chatillon crush strength analyzer (Model DPP 50). The force necessary for failure in 25 measurements of ⅛ inch long extrudates is averaged to give the reported value. Bulk density is measured by placing 40 g of the catalyst in a 100-mL graduated cylinder (1" nominal outer, diameter). The graduated cylinder is tapped until the apparent volume no longer changes, and then this value is divided into the mass to calculate the bulk density. Voidage is determined by adding the pellets to 50 mL water in a second graduated cylinder and then tapping until all voids are filled. The resulting water level is subtracted from the total volume of the water and the pellets taken separately to determine the void volume occupied by water. Total pore volume is determined by pouring the mixture through a sieve basket, shaking to remove excess water and then weighing the wet extrudates. The increase in mass over the initial 40 g of the catalyst divided by the density of water is taken as the measure of the pore volume.

Vinyl Acetate Production:

The palladium-gold catalyst is tested for vinyl acetate production in a fixed-bed reactor (stainless steel, 1 inch O.D.). The reactor is charged with a mixture of the catalyst (10 g) and an inert alpha alumina cylindrical pellets (⅛" in diameter, surface area 4 $m^2$/g, pore volume 0.25 mL/g, 25 g). The feed contains 46.1 mol % helium, 33.9 mol % ethylene, 11.48 mol % acetic acid, 4.2 mol % oxygen, and 4.2 mol % nitrogen. The reactor pressure is 80 psig and the space velocity relative to the volume of the catalyst is 3050 $h^{-1}$ at standard temperature and pressure. The reactor is cooled using a fluidized sand bath, the temperature of which is set at 130° C. The product stream is analyzed by gas chromatography (GC). Oxygen conversion, oxygen selectivity, oxygen yield to vinyl acetate, and ethylene selectivity to vinyl acetate between 40 to 50 h on stream are calculated from the GC results and listed in Table 1. Oxygen conversion is calculated by dividing the amount of oxygen consumed by the total amount of oxygen fed to the reactor. Oxygen selectivity to vinyl acetate is the amount of oxygen consumed in making vinyl acetate divided by the total amount of oxygen consumed. Oxygen yield to vinyl acetate is the product of oxygen conversion multiplied by oxygen selectivity. Ethylene selectivity to vinyl acetate is the amount of ethylene consumed in making vinyl acetate divided by the total amount of ethylene consumed. Catalyst productivity is the grams of vinyl acetate produced per liter of the catalyst per hour.

Example 2 and Comparative Examples 3, 4

The procedure of Example 1 is repeated with the formulation shown in Table 1.

Table 1 and FIG. 1 show palladium-gold catalysts supported on titania-alumina extrudates with 1 and 10 wt % alumina have similar porosities as those supported on a titania extrudate, but with increased surface areas and improved activities, and significantly higher crush strength than the one prepared from titania extrudate (Comparative Example 4).

However, the catalyst prepared from an extrudate containing 20 wt % alumina and 80 wt % titania gives lower productivity in vinyl acetate production than that prepared from a titania extrudate, even though it has a larger surface area. The low activity obtained in Comparative Example 3 may be due to the formation of smaller pores as indicated by its larger surface area.

TABLE 1

| Example | 1 | 2 | C. 3 | C. 4 |
|---|---|---|---|---|
| Extrudate formulation | | | | |
| DT-51 titania (g) | 178.2 | 162.0 | 144.0 | 180.0 |
| DISPERAL ® P2 alumina (g) | 1.8 | 18.0 | 36.0 | 0 |
| Extrudate composition | | | | |
| Titania (wt %) | 99 | 90 | 80 | 100 |
| Alumina (wt %) | 1 | 10 | 20 | 0 |
| Catalyst characterization | | | | |
| Crush strength (lb per 1/8 inch) | 10.0 | 19.3 | 25.1 | 5.5 |
| Porosity (mL per 100 g) | 45.4 | 47.4 | 45.8 | 47.8 |
| Surface area ($m^2/g$) | 48 | 61 | 101 | 35 |
| Catalyst performance | | | | |
| Oxygen conversion (%) | 71.8 | 67.8 | 53.4 | 66.2 |
| Oxygen selectivity to vinyl acetate (%) | 84.1 | 84.5 | 85.6 | 84.9 |
| Oxygen yield to vinyl acetate (%) | 60.4 | 57.3 | 45.7 | 56.2 |
| Ethylene selectivity to vinyl acetate (%) | 96.9 | 96.9 | 97.2 | 97.1 |
| Catalyst productivity ($g \cdot L^{-1} \cdot h^{-1}$) | 498.7 | 473.1 | 377.3 | 464.0 |

I claim:

1. An acetoxylation catalyst comprising:
   (a) palladium and
   (b) an extrudate wherein the extrudate comprises
      (i) at least 80 wt % titania and 0.1 to 15 wt % alumina; and
      (ii) cellulose
   wherein the palladium is supported on the extrudate.

2. The catalyst of claim 1 wherein the extrudate comprises 0.2 to 10 wt % alumina.

3. The catalyst of claim 1 wherein the extrudate comprises 0.5 to 5 wt % alumina.

4. The catalyst of claim 1 further comprising a Group 11 metal.

5. The catalyst of claim 4 wherein the Group 11 metal is gold.

6. The catalyst of claim 1 wherein the amount of palladium is 0.05 to 3 wt % of the catalyst.

7. The catalyst of claim 1 wherein the extrudate is produced by using an extrusion aid comprising a carboxyalkyl cellulose and a hydroxyalkyl cellulose.

8. The catalyst of claim 7 wherein the weight ratio of the carboxyalkyl cellulose to the hydroxyalkyl cellulose is from 3:1 to 1:1.

9. The catalyst of claim 7 wherein the hydroxyalkyl cellulose is selected from the group consisting of methyl 2-hydroxypropyl cellulose, methyl 2-hydroxyethyl cellulose, and mixtures thereof.

10. The catalyst of claim 1 wherein the extrudate is calcined at a temperature of 650 to 750° C.

11. A process for preparing vinyl acetate comprising reacting ethylene, oxygen, and acetic acid in the presence of the catalyst of claim 1.

12. The process of claim 11 wherein the extrudate comprises 0.2 to 10 wt % alumina.

13. The process of claim 11 wherein the extrudate comprises 0.5 to 5 wt % alumina.

14. The process of claim 11 wherein the catalyst of claim 1 further comprises a Group 11 metal.

15. The process of claim 14 wherein the Group 11 metal is gold.

* * * * *